United States Patent

De Nanteuil et al.

Patent Number: 6,066,633
Date of Patent: May 23, 2000

[54] METALLOPROTEINASE INHIBITORS

[75] Inventors: Guillaume De Nanteuil, Suresnes; Georges Remond, Versailles; Joseph Paladino, Conflans Sainte Honorine; Ghanem Atassi, Saint Cloud; Alain Pierre, Les Alluets le Roi; Gordon Tucker; Jacqueline Bonnet, both of Paris; Massimo Sabatini, Garches, all of France

[73] Assignee: Adir et Compagnie, Courbevoie, France

[21] Appl. No.: 09/191,323

[22] Filed: Nov. 13, 1998

[30] Foreign Application Priority Data

Nov. 14, 1997 [FR] France ................... 97.14278

[51] Int. Cl.[7] .............. A61K 31/5377; A61K 31/4523; C07D 487/44

[52] U.S. Cl. ............ 514/232.8; 514/292; 544/126; 546/86; 546/87

[58] Field of Search .............. 544/126; 546/86, 546/87; 514/232.8, 292

[56] References Cited

U.S. PATENT DOCUMENTS 5,643,916  7/1997  Audin et al. ............... 514/285

OTHER PUBLICATIONS

Harris, Adrian L., "Antiangiogenesis for Cancer Therapy", The Lancet, vol. 349 (1997) pp. 13–15.

Skobe, Mihaela, et al., "Halting Angiogenesis Suppresses Carcinoma Cell Invasion", Nature Medicine, vol. 3 No. 11, (1997) pp. 1222–1227.

Kleiner, David E., et al., "Matrix Metalloproteinases and Metastasis", Cancer Chemother Pharmacol, vol. 43 (Suppl) (1999) pp. S42–S51.

Nemunaitis, John et al., "Combined Analysis of Studies of the Effects of the Matrix Metallo–proteinase Inhibitor Marimastat on Serum Tumor Markers in Advanced Cancer: Selection of a Biologically Active and Tolerable Dose for Longer–Term Studies", Clinical Cancer Research, vol. 4 (1998) pp. 1101–1109.

Steward, William P., "Marimastat (BB2516): Current Status of Development", Cancer Chemother Pharnacol, vol. 43 (Suppl) (1999) pp. S56–S60.

*Primary Examiner*—Patricia L. Morris
*Attorney, Agent, or Firm*—The Firm of Gordon W. Hueschen

[57] ABSTRACT

Compound of formula (I):

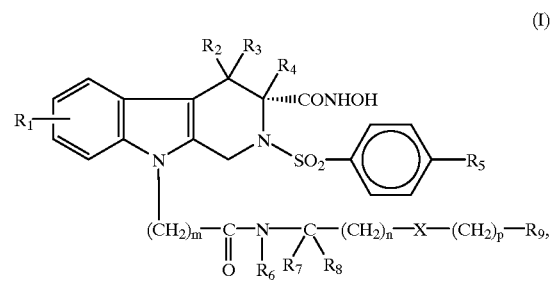

in which:
- m represents an integer from 1 to 4 inclusive, and n and p an integer from 0 to 4 inclusive,
- X represents O, S or a single bond,
- $R_1$ represent hydrogen or halogen, or alkyl, alkoxy, hydroxy, trihaloalkyl or trihaloalkoxy,
- $R_2$, $R_3$ and $R_4$, which may be same or different, each represents hydrogen or alkyl,
- $R_5$ represents hydrogen or halogen, or alkoxy, aryloxy or heteroaryloxy,
- $R_6$, $R_7$ and $R_8$, which may be same or different, each represents hydrogen or alkyl, or together form, with the atoms carrying them respectively, an optionally substituted heterocycle,
- $R_9$ represents $SO_3H$, $-CO_2R_{10}$, $-CO-NR_{11}R_{12}$, or $-NR_{13}R_{14}$, wherein $R_{10}$, $R_{11}$, $R_{12}$, $R_{13}$ and $R_{14}$ each represents hydrogen or alkyl or together ($R_{11}/R_{12}$; $R_{13}/R_{14}$) form, with nitrogen carrying them, heterocycle, isomers thereof, and addition salts thereof with a pharmaceutically-acceptable acid or base.

11 Claims, No Drawings

METALLOPROTEINASE INHIBITORS

FIELD OF THE INVENTION

The present invention relates to new metalloproteinase inhibitors.

DESCRIPTION OF THE PRIOR ART

In the physiological state, the synthesis of connective tissues is in dynamic equilibrium with the degradation of the extracellular matrix. That degradation is due to zinc proteinases (metalloproteinases) secreted by the cells of the existing matrix; those proteinases are, without implying any limitation, collagenases (MMP-1), gelatinases or collagenases of type IV (MMP-2, MMP-9) and stromelysins (MMP-3).

In the normal state, those catabolic enzymes are regulated in terms of their synthesis and their secretion, as well as in terms of their extracellular enzymatic activity, by natural inhibitors, such as $\alpha_2$-macroglobulin or the TIMPs (Tissue Inhibitors of MetalloProteinases), which form inactive complexes with the metalloproteinases.

A common factor in the pathologies in which those enzymes are implicated is an imbalance between the activity of the activated enzymes and that of their natural inhibitors, the consequence of which is excessive tissue degradation.

Uncontrolled and accelerated membrane degradation by resorption of the extracellular matrix catalysed by the metalloproteinases is a parameter common to a number of pathological conditions, such as rheumatoid arthritis, arthrosis, tumour invasion and growth, including malignant dissemination and the formation of metastases, ulceration, atherosclerosis etc.

BB94, a metalloproteinase inhibitor, has recently exhibited anti-tumour activity in clinical use, where it has proved to be active in ovarian cancers (Becket et al., DDT 1996, 1 (1), 16).

It may therefore be expected that a metalloproteinase inhibitor will restore the equilibrium between proteinase and inhibitor and, as a result, favourably modify the development of those pathologies.

A certain number of metalloproteinase inhibitors have been described in the literature, especially the compounds described in Patent Applications WO 95/35275, WO 95/35276, EP 606 046 and WO 96/00214.

The compounds of the invention are not only new but have also proved to be metalloproteinase inhibitors, making them potentially useful in the treatment of cancers, rheumatic diseases, such as arthrosis and rheumatoid arthritis, atherosclerosis etc.

DETAIL DESCRIPTION OF THE INVENTION

More specifically, the present invention relates to the compounds of formula (I):

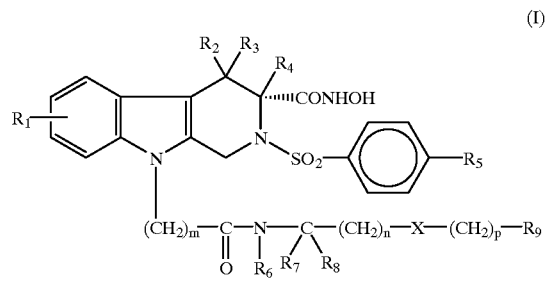

in which:
  m represents an integer from 1 to 4 inclusive,
  n and p, which may be the same or different, each represents independently of the other an integer from 0 to 4 inclusive,
  X represents an oxygen or sulphur atom or a single bond,
  $R_1$ represents a hydrogen atom, a halogen atom, a linear or branched $(C_1-C_6)$alkyl group, a linear or branched $(C_1-C_6)$trihaloalkyl group, a hydroxy group, a linear or branched $(C_1-C_6)$alkoxy group or a linear or branched $(C_1-C_6)$trihaloalkoxy group,
  $R_2$, $R_3$ and $R_4$, which may be the same or different, each represents independently of the others a hydrogen atom or a linear or branched $(C_1-C_6)$alkyl group,
  $R_5$ represents a hydrogen atom, a halogen atom, a linear or branched $(C_1-C_6)$alkoxy group, an aryloxy group or a heteroaryloxy group,
  $R_6$, $R_7$ and $R_8$, which may be the same or different, each represents independently of the others a hydrogen atom or a linear or branched $(C_1-C_6)$alkyl group, or together ($R_6$ and $R_7$ or $R_6$ and $R_8$) form, with the nitrogen atom carrying the group $R_6$ and the carbon atom carrying the groups $R_7$ and $R_8$, an optionally substituted heterocycle, the remaining group ($R_8$ or $R_7$, respectively) then having one of the meanings given above,
  $R_9$ represents any one of the following groups:
    —$SO_3H$,
    —$CO_2R_{10}$ in which $R_{10}$ represents a hydrogen atom or a linear or branched $(C_1-C_6)$alkyl group,
    —CO—$NR_{11}R_{12}$ in which $R_{11}$ and $R_{12}$, which may be the same or different, each represents a hydrogen atom or a linear or branched $(C_1-C_6)$alkyl group, or $R_{11}$ and $R_{12}$ together form, with the nitrogen atom carrying them, an optionally substituted heterocycle,
    —$NR_{13}R_{14}$ in which $R_{13}$ and $R_{14}$, which may be the same or different, each represents a hydrogen atom or a linear or branched $(C_1-C_6)$alkyl group, or $R_{13}$ and $R_{14}$ together form, with the nitrogen atom carrying them, an optionally substituted heterocycle,
their isomers, and addition salts thereof with a pharmaceutically acceptable acid or base.
  It must be understood that:
    an aryl group is taken to mean a phenyl, naphthyl, dihydronaphthyl or tetrahydronaphthyl group, each of those groups being optionally substituted by one or more, identical or different, groups selected from halogen, linear or branched $(C_1-C_6)$alkyl, linear or branched $(C_1-C_6)$trihaloalkyl, linear or branched ($C_1$–$C_6$)alkoxy, linear or branched ($C_1$–$C_6$) trihaloalkoxy or hydroxy, a heteroaryl group is taken to mean an aryl group that is optionally substituted by one or more groups as defined above and that contains one, two or three, identical or different, hetero atoms selected from oxygen, nitrogen or sulphur, a heterocycle is taken to mean a saturated or unsaturated, mono- or bi-cyclic, 4- to 7-membered group containing one, two or three, identical or different, hetero atoms selected from oxygen, nitrogen or sulphur, it being possible for the said heterocycle optionally to be substituted by one or more, identical or different, groups selected from halogen, linear or branched ($C_1$–$C_6$) alkyl, linear or branched ($C_1$–$C_6$)alkoxy, hydroxy, amino (optionally substituted by one or two linear or branched ($C_1$–$C_6$)alkyl groups, which may be the same or different) or by a heterocycle.

Among the pharmaceutically acceptable acids there may be mentioned by way of non-limiting example hydrochloric, hydrobromic, sulphuric, phosphonic, acetic, trifluoroacetic, lactic, pyruvic, malonic, succinic, glutaric, fumaric, tartaric, maleic, citric, ascorbic, oxalic, methanesulphonic, camphoric acid etc.

Among the pharmaceutically acceptable bases there may be mentioned by way of non-limiting example sodium hydroxide, potassium hydroxide, triethylamine, tert-butylamine etc.

The invention extends also to the process for the preparation of the compounds of formula (I), characterised in that there is used as starting material a D-tryptophan compound, in racemic form or in the form of a pure enantiomer, of formula (II):

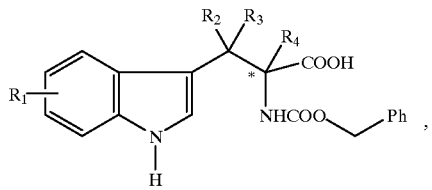

(II)

in which $R_1$, $R_2$, $R_3$ and $R_4$ are as defined in formula (I), the amine function of the indole ring system of which is substituted by a halogenated compound of formula (III):

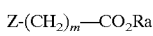

Z-(CH$_2$)$_m$—CO$_2$Ra         (III), in which m is as defined in formula (I), Z represents a halogen atom and Ra represents a linear or branched ($C_1$–$C_6$)alkyl group, to yield a compound of formula (IV):

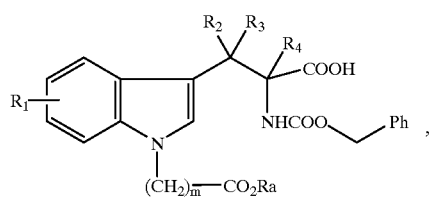

(IV)

in which $R_1$, $R_2$, $R_3$, $R_4$, Ra and m are as defined above, the amine function of the side chain of which compound of formula (IV) is deprotected by a catalytic hydrogenation reaction to yield a compound of formula (V):

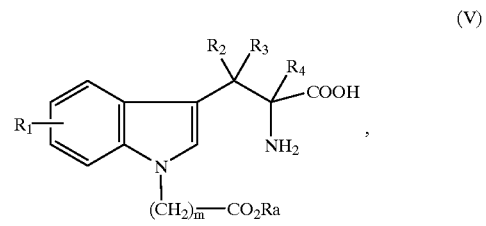

(V)

in which $R_2$, $R_2$, $R_3$, $R_4$, Ra and m are as defined above, which is cyclised, in the presence of a strong acid and formaldehyde, to yield a compound of formula (VI):

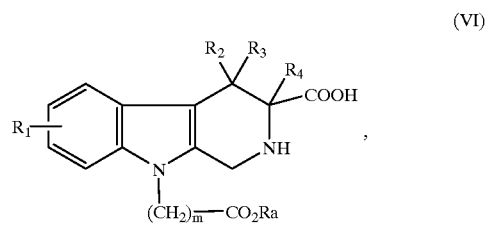

(VI)

in which $R_1$, $R_2$, $R_3$, $R_4$, Ra and m are as defined above, which compound of formula (VI) is condensed, in a basic medium, with a halogenated compound of formula (VII):

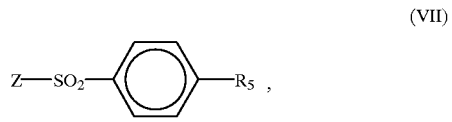

(VII)

in which $R_5$ is as defined in formula (I) and Z represents a halogen atom, to yield a compound of formula (VIII):

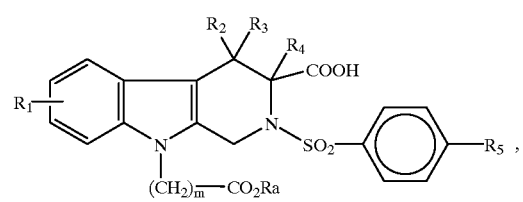

(VIII)

in which $R_1$, $R_2$, $R_3$, $R_4$, $R_5$, Ra and m are as defined above, which is condensed, in a basic medium and in the presence of dicyclohexylcarbodiimide, with an O-substituted hydroxylamine of formula (IX):

H$_2$N—O—R$_{15}$         (IX), in which $R_{15}$ represents an allyl or benzyl group, to yield a compound of formula (X):

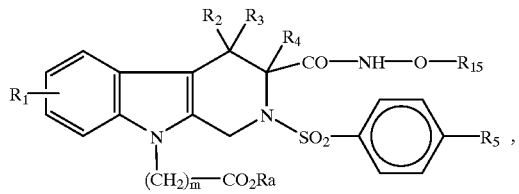

in which $R_1$, $R_2$, $R_3$, $R_4$, $R_5$, $R_{15}$, Ra and m are as defined above, the carboxylic acid function of which is deprotected, in the presence, for example, of trifluoroacetic acid, to yield a compound of formula (XI):

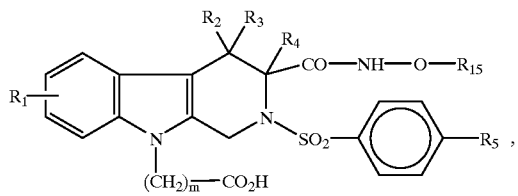

in which $R_1$, $R_2$, $R_3$, $R_4$, $R_5$, $R_{15}$ and m are as defined above, which is condensed with an amine of formula (XII):

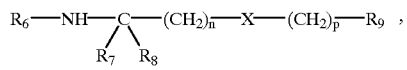

in which $R_6$, $R_7$, $R_8$, $R_9$, n and p are as defined in formula (I), to yield a compound of formula (XIII):

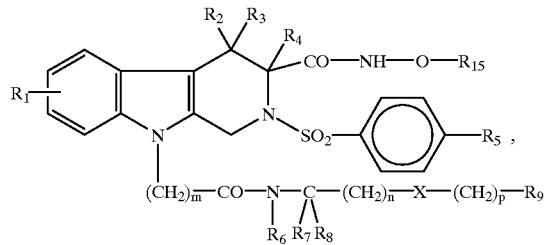

in which $R_1$, $R_2$, $R_3$, $R_4$, $R_5$, $R_6$, $R_7$, $R_8$, $R_9$, $R_{15}$, m, n and p are as defined above, the hydroxylamine function of which compound of formula (XIII) is deprotected to yield the compound of formula (I):

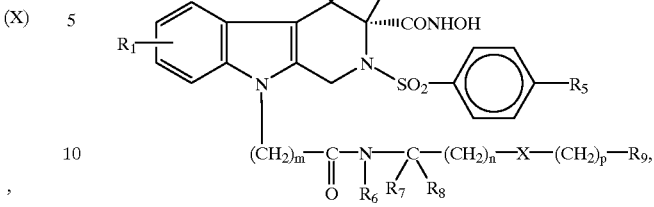

in which $R_1$, $R_2$, $R_3$, $R_4$, $R_5$, $R_6$, $R_7$, $R_8$, $R_9$, m, n and p are as defined above, which compounds of formula (I) are, if necessary, purified according to a conventional purification technique, are, where appropriate, separated into their isomers according to a conventional separation technique and are, if desired, converted into their addition salts with a pharmaceutically acceptable acid or base.

The compounds of formulae (II), (III), (VII), (IX) and (XII) are either commercial products or are obtained according to conventional methods of organic synthesis.

The invention extends also to pharmaceutical compositions comprising as active ingredient at least one compound of formula (I), its optical isomers or an addition salt thereof with a pharmaceutically acceptable acid or base, alone or in combination with one or more pharmaceutically acceptable, inert, non-toxic excipients or carriers. Among the pharmaceutical compositions according to the invention there may be mentioned more especially those that are suitable for oral, parenteral (intravenous, intramuscular or subcutaneous), nasal, rectal, per- or trans-cutaneous, perlingual, ocular or respiratory administration, and especially tablets, dragees, sublingual tablets, soft gelatin capsules, hard gelatin capsules, suppositories, creams, ointments, dermal gels, injectable preparations, drinkable suspensions, aerosols, eye or nose drops etc.

The useful dosage can be adapted according to the nature and severity of the disorder, the route of administration, the administration of any associated treatments, and also the age and the weight of the patient. The dosage varies from 0.01 g to 2 g in one or more administrations per day.

The Examples which follow illustrate the invention but do not limit it in any way.

The starting materials used are materials that are known or prepared according to known procedures.

Preparations A to G yield synthesis intermediates that are useful in the preparation of the compounds of the invention.

The structures of the compounds described in the Examples and the Preparations have been determined according to customary spectrophotometric techniques (infrared, NMR, mass spectrometry, . . . ).

EXAMPLE 1

2-[(4-Methoxyphenyl)sulphonyl]-9-[(3-morpholin-4-ylpropylcarbamoyl)methyl]-2,3,4,9-tetrahydro-1H-β-carboline-(3R)-(N-hydroxy)carboxamide Hydrochloride Step A 1-[(tert-Butoxycarbonyl)methyl]-Nα-benzyloxycarbonyl-D-tryptophan 600 ml of a solution of NaHMDS (sodium salt of 1,1,1,3,3,3-hexamethyldisilazane) (1M) in tetrahydrofuran are added dropwise, at −78° C. under an inert atmosphere, to a solution of 100 g of Nα-benzyloxycarbonyl-D-tryptophan in a liter of anhydrous tetrahydrofuran. After one hour, the temperature is brought to 0° C. and a solution of 64 g of tert-butyl bromoacetate in 50 ml of anhydrous tetrahydrofuran is added dropwise. The reaction mixture is then brought to ambient temperature and the solvent is subsequently evaporated off in vacuo. The residue is diluted with dichloromethane and the solution is acidified by adding an aqueous 4N hydrochloric acid solution. After extraction with dichloromethane, the organic phases are dried over sodium sulphate and then concentrated in vacuo. 136 g of the expected product are obtained.

Step B

1-[(tert-Butoxycarbonyl)methyl]-D-tryptophan

The 136 g of product obtained in Step A are diluted with 1.5 liters of methanol and hydrogenated in the presence of 5 g of 10% Pd/C under an $H_2$ pressure of 1.2 bars. After 12 hours of reaction at ambient temperature, the solution is filtered and then concentrated in vacuo. 87 g of the expected product are obtained in the form of a beige powder.

Melting point: 260° C.

Step C

9-[(tert-Butoxycarbonyl)methyl]-2,3,4,9-tetrahydro-β-carboline-(3R)-carboxylic Acid To a suspension of 85 g of the product of Step B in 600 ml of water there are added 130 ml of a 0.1N sulphuric acid solution and then, dropwise, 130 ml of a 37% formaldehyde solution. After 48 hours of reaction at ambient temperature, the reaction mixture is filtered, washed with water and then dried over $P_2O_5$. 82.6 g of a white solid corresponding to the expected product are obtained.

Melting point: 230° C.

Step D

9-[(tert-Butoxycarbonyl)methyl]-2-[(4-methoxyphenyl)sulphonyl]-2,3,4,9-tetrahydro-1H-β-carboline-(3R)-carboxylic Acid 750 ml of water and then 85 ml of triethylamine are added to a solution of 80 g of the product of Step C in 1.5 liters of dioxane. The reaction mixture is cooled to 0° C. and 60 g of 4-methoxybenzenesulphonyl chloride diluted with 100 ml of dioxane are added dropwise. The reaction mixture is then brought to ambient temperature and stirring is carried out for 12 hours. After evaporating off the dioxane in vacuo, the residual solution is diluted with water and then acidified by adding a 4N hydrochloric acid solution and extracted with dichloromethane. The combined organic phases are subsequently washed with water and then with a saturated NaCl solution, dried over sodium sulphate and concentrated in vacuo. The residue is crystallised from pentane, allowing 115.2 g of the desired product to be obtained in the form of a white powder.

Melting point: 150° C.

Step E

9-[(tert-Butoxycarbonyl)methyl]-2-[(4-methoxyphenyl)sulphonyl]-2,3,4,9-tetrahydro-1H-β-carboline-(3R)-(N-allyloxy)carboxamide 24.1 g of O-allylhydroxylamine, 27 g of hydroxybenzotriazole, 41.2 g of dicyclohexylcarbodiimide and 31 ml of triethylamine are added at 0° C. to a solution of 100 g of the compound of Step D in 1.5 liters of dimethylformamide. After 12 hours' stirring at ambient temperature, the reaction mixture is concentrated in vacuo. The residue is diluted with ethyl acetate and then washed, in succession, with a 10% aqueous sodium hydrogen carbonate solution, water and a saturated sodium chloride solution. The organic phase is then dried over sodium sulphate and evaporated, yielding 120 g of the expected product in the form of an oil.

Step F

2-[(4-Methoxyphenyl)sulphonyl]-2,3,4,9-tetrahydro-1H-β-carboline-(3R)-[(N-allyloxy)carboxamide]-9-ethanoic Acid 70 ml of trifluoroacetic acid are added at 0° C. to a solution of 50 g of the compound of Step E in 500 ml of anhydrous dichloromethane. After 12 hours at ambient temperature, the reaction mixture is concentrated in vacuo and the residue obtained is crystallised from ethyl ether, yielding 30.8 g of desired product in the form of a beige solid.

Melting point: 160° C.

Step G

2-[(4-Methoxyphenyl)sulphonyl]-9-[(3-morpholin-4-ylpropylcarbamoyl)methyl]-2,3,4,9-tetrahydro-1H-β-carboline-(3R)-N-allyloxy)carboxamide 1 ml of N-(3-aminopropyl)morpholine, 0.95 g of hydroxybenzotriazole and 1.5 g of dicyclohexylcarbodiimide are added at 0° C. to a solution of 3.5 g of the compound of Step F in 50 ml of dimethylformamide. After 12 hours at ambient temperature, the reaction mixture is first filtered in order to remove excess dicyclohexylcarbodiimide and then concentrated in vacuo. The residue is diluted with dichloromethane, washed three times with water and then with a saturated sodium chloride solution; the organic phase is subsequently dried over sodium sulphate and then evaporated under reduced pressure. The expected product is subsequently isolated by chromatography on silica gel (eluant: dichloromethane/methanol/ammonium hydroxide:95/5/0.5).

Step H

2-[(4-Methoxyphenyl)sulphonyl]-9-[(3-morpholin-4-ylpropylcarbamoyl)methyl]-2,3,4,9-tetrahydro-1H-β-carboline-(3R)-(N-hydroxy)carboxamide Hydrochloride 0.7 ml of acetic acid and 0.14 g of $Pd(PPh_3)_2Cl_2$ are added, at ambient temperature and under an inert atmosphere, to a solution of 2.5 g of the compound obtained in Step G in 50 ml of dichloromethane. After 5 minutes, 2.3 ml of tri-n-butyltin hydride are added and the reaction mixture is maintained at ambient temperature for one hour and then evaporated to dryness. The residue is then diluted with hexane. A precipitate is formed, which is filtered off, diluted with an aqueous hydrochloric acid solution; the latter is then washed with water and then with hexane. After filtration and lyophilisation, 2 g of the expected product are obtained.

|  | Elemental microanalysis: | | | | |
| --- | --- | --- | --- | --- | --- |
|  | C | H | N | Cl | S |
| % Calculated | 54.06 | 5.83 | 11.26 | 5.70 | 5.15 |
| % Found | 54.28 | 5.98 | 11.29 | 5.88 | 4.87 |

EXAMPLE 2

2-[(4-Methoxyphenyl)sulphonyl]-9-[(2-morpholin-4-ylethylcarbamoyl)methyl]-2,3,4,9-tetrahydro-1H-β-carboline-(3R)-(N-hydroxy)carboxamide Acetate The expected product is obtained according to the same process as that described in Example 1 using N-(2-aminopropyl)morpholine as reagent in Step G.

|  | Elemental microanalysis: | | | |
| --- | --- | --- | --- | --- |
|  | C | H | N | S |
| % Calculated | 55.14 | 5.90 | 11.09 | 5.08 |
| % Found | 54.79 | 6.06 | 10.89 | 4.99 |

EXAMPLE 3

2-[(4-Methoxyphenyl)sulphonyl]-9-[(4-morpholin-4-ylbutylcarbamoyl)methyl]-2,3,4,9-tetrahydro-1H-β-carboline-(3R)-(N-hydroxy)carboxamide Hydrochloride The expected product is obtained according to the same process as that described in Example 1 using N-(4-aminobutyl)morpholine as reagent in Step G.

|  | Elemental microanalysis: | | | | |
| --- | --- | --- | --- | --- | --- |
|  | C | H | N | Cl | S |
| % Calculated | 54.75 | 6.02 | 18.01 | 5.57 | 5.04 |
| % Found | 54.53 | 6.27 | 10.58 | 5.75 | 5.23 |

EXAMPLE 4

2-[(4-Methoxyphenyl)sulphonyl]-3-methyl-9-[(2-morpholin-4-ylethylcarbamoyl)methyl]-2,3,4,9-tetrahydro-1H-β-carboline-(3R)-(N-hydroxy)carboxamide Hydrochloride The expected product is obtained according to the same process as that described in Example 1 using 2-[(benzyloxycarbonyl)amino]-2-methyl-3-(1H-3-indolyl)-(2R)-propanoic acid as substrate in Step A and using in Step G the reagent used in Example 2.

EXAMPLE 5

2-[(4-Methoxyphenyl)sulphonyl]-3-methyl-9-[(3-morpholin-4-ylpropylcarbamoyl)methyl]-2,3,4,9-tetrahydro-1H-β-carboline-(3R)-(N-hydroxy)carboxamide Hydrochloride The expected product is obtained according to the same process as that describe in Example 1 using as substrate in Step A the compound used in Step A of Example 4.

EXAMPLE 6

2-[(4-Methoxyphenyl)sulphonyl]-4,4-dimethyl-9-[(2-morpholin-4-ylethylcarbamoyl)methyl]-2,3,4,9-tetrahydro-1H-β-carboline-3R)-(N-hydroxy)carboxamide Hydrochloride The expected product is obtained according to the same process as that described in Example 1 using 2-[(benzyloxycarbonyl)amino]-3-methyl-3-(1H-3-indolyl)-(2R)-butanoic acid as substrate in Step A and using in Step G the reagent used in Example 2.

EXAMPLE 7

2-[(4-Methoxyphenyl)sulphonyl]-4,4-dimethyl-9-[(3-morpholin-4-ylpropylcarbamoyl)methyl]-2,3,4,9-tetrahydro-1H-β-carboline-(3R)-(N-hydroxy)carboxamide Hydrochloride The expected product is obtained according to the same process as that described in Example 1 using in Step A the substrate used in Example 6.

EXAMPLE 8

2-{[4-(4-Pyridyloxy)phenyl]sulphonyl}-9-[(2-morpholin-4-ylethylcarbamoyl)methyl]-2,3,4,9-tetrahydro-1H-β-carboline-(3R)-(N-hydroxy)carboxamide The expected product is obtained according to the same process as that described in Example 1 using 4-(4-pyridyloxy)-benzenesulphonic chloride as reagent in Step D and using the reagent of Example 2 in Step G.

EXAMPLE 9

2-{[4-(4-Pyridyloxy)phenyl]sulphonyl}-9-[(3-morpholin-4-ylpropylcarbamoyl)methyl]-2,3,4,9-tetrahydro-1H-β-carboline-(3R)-(N-hydroxy)carboxamide Hydrochloride The expected product is obtained according to the same process as that described in Example 1 using the reagent of Example 8 in Step D.

EXAMPLE 10

2-[(4-Methoxyphenyl)sulphonyl]-9-(2-[1,4']-bipiperidin-1'-yl-2-oxoethyl)-2,3,4,9-tetrahydro-1H-β-carboline-(3R)-(N-hydroxy)carboxamide Hydrochloride The expected product is obtained according to the same process as that described in Example 1 using [1,4']-bipiperidine as reagent in Step G.

|  | Elemental microanalysis: | | | | |
| --- | --- | --- | --- | --- | --- |
|  | C | H | N | Cl | S |
| % Calculated | 57.62 | 6.24 | 10.84 | 5.49 | 4.96 |
| % Found | 57.58 | 6.13 | 10.49 | 5.72 | 4.86 |

EXAMPLE 11

2-[(4-Methoxyphenyl)sulphonyl]-9-{[2-(2-morpholin-4-ylethylsulphanyl)ethylcarbamoyl]methyl}-2,3,4,9-tetrahydro-1H-β-carboline-(3R)-(N-hydroxy)carboxamide Hydrochloride The expected product is obtained according to the same process as that described in Example 1 using 2-[(2-morpholinoethyl)sulphanyl]ethylamine as reagent in Step G.

| | Elemental microanalysis: | | | | |
|---|---|---|---|---|---|
| | C | H | N | Cl | S |
| % Calculated | 52.13 | 5.73 | 10.48 | 5.31 | 9.60 |
| % Found | 52.80 | 5.80 | 10.33 | 5.20 | 9.34 |

EXAMPLE 12

2-[(4-Methoxyphenyl)sulphonyl]-9-{[3-(3-morpholin-4-ylpropylsulphanyl)propylcarbamoyl]methyl}-2,3,4,9-tetrahydro-1H-β-carboline-(3R)-(N-hydroxy)carboxamide Hydrochloride The expected product is obtained according to the same process as that described in Example 1 using 3-[(3-morpholinopropyl)sulphanyl]propylamine as reagent in Step G.

| | Elemental microanalysis: | | | | |
|---|---|---|---|---|---|
| | C | H | N | Cl | S |
| % Calculated | 53.48 | 6.08 | 10.06 | 5.09 | 9.21 |
| % Found | 53.10 | 6.04 | 9.60 | 5.05 | 8.95 |

EXAMPLE 13

2-[(4-Methoxyphenyl)sulphonyl]-9-{[2-(3-morpholin-4-ylpropylsulphanyl)ethylcarbamoyl]methyl}-2,3,4,9-tetrahydro-1H-β-carboline-(3R)-(N-hydroxy)carboxamide Hydrochloride The expected product is obtained according to the same process as that described in Example 1 using 2-[(3-morpholinopropyl)sulphanyl]ethylamine as reagent in Step G.

| | Elemental microanalysis: | | | | |
|---|---|---|---|---|---|
| | C | H | N | Cl | S |
| % Calculated | 52.81 | 5.91 | 10.26 | 5.20 | 9.40 |
| % Found | 52.88 | 5.79 | 9.98 | 5.25 | 9.06 |

EXAMPLE 14

2-[(4-Methoxyphenyl)sulphonyl]-9-{[3-(2-morpholin-4-ylethylsulphanyl)propylcarbamoyl]methyl}-2,3,4,9-tetrahydro-1H-β-carboline-(3R)-(N-hydroxy)carboxamide Hydrochloride The expected product is obtained according to the same process as that described in Example 1 using 3-[(2-morpholinoethyl)sulphanyl]propylamine as reagent in Step G.

| | Elemental microanalysis: | | | | |
|---|---|---|---|---|---|
| | C | H | N | Cl | S |
| % Calculated | 52.81 | 5.91 | 10.26 | 5.20 | 9.40 |
| % Found | 53.35 | 5.88 | 10.12 | 5.21 | 9.11 |

EXAMPLE 15

2-[(4-Methoxyphenyl)sulphonyl]-9-[N-methyl-(2-morpholin-4-ylethylcarbamoyl)methyl]-2,3,4,9-tetrahydro-1H-β-carboline-(3R)-(N-hydroxy)carboxamide Hydrochloride The expected product is obtained according to the same process as that described in Example 1 using N-methyl-3-(aminopropyl)morpholine as reagent in Step G.

| | Elemental microanalysis: | | | | |
|---|---|---|---|---|---|
| | C | H | N | Cl | S |
| % Calculated | 54.06 | 5.83 | 11.26 | 5.70 | 5.15 |
| % Found | 54.32 | 5.81 | 10.86 | 5.81 | 4.68 |

EXAMPLE 16

2-[(4-Methoxyphenyl)sulphonyl]-9-[(2-sulphoethylcarbamoyl)methyl]-2,3,4,9-tetrahydro-1H-β-carboline-(3R)-(N-hydroxy)carboxamide The expected product is obtained according to the same process as that described in Example 1 using 2-aminoethylsulphonic acid as reagent in Step G.

Mass spectrometry: [M-H]=565

EXAMPLE 17

2-[(4-Methoxyphenyl)sulphonyl]-9-[(1,1-dimethyl-(2-morpholin-4-yl)ethylcarbamoyl)methyl]-2,3,4,9-tetrahydro-1H-β-carboline-(3R)-(N-hydroxy)carboxamide Hydrochloride The expected product is obtained according to the same process as that described in Example 1 using N-[(2-amino-2-methyl)propyl]morpholine as reagent in Step G.

Elemental microanalysis:

| | C | H | N | Cl | S |
|---|---|---|---|---|---|
| % Calculated | 54.75 | 6.02 | 11.01 | 5.57 | 5.04 |
| % Found | 55.16 | 6.22 | 11.17 | 5.36 | 4.78 |

EXAMPLE 18

6-Hydroxy-2-[(4-methoxyphenyl)sulphonyl]-9-[(3-carboxypropylcarbamoyl)methyl]-2,3,4,9-tetrahydro-1H-β-carboline-(3R)-(N-hydroxy)carboxamide Dihydrochloride The expected product is obtained according to the same process as that described in Example 1 using N-benzyloxycarbonyl-5-hydroxy-D-tryptophan as substrate in Step A and 4-aminobutanoic acid as reagent in Step G.

EXAMPLE 19

6-Methoxy-2-[(4-methoxyphenyl)sulphonyl]-9-[(3-carbamoylpropylcarbamoyl)methyl]-2,3,4,9-tetrahydro-1H-β-carboline-(3R)-(N-hydroxy)carboxamide Hydrochloride The expected product is obtained according to the same process as that described in Example 1 using N-benzyloxycarbonyl-5-methoxy-D-tryptophan as substrate in Step A and 4-aminobutylamide in Step G.

EXAMPLE 20

6-Methoxy-2-[(4-methoxyphenyl)sulphonyl]-9-{[(4-(N,N-dimethyl)carbamoyl)butylcarbamoyl]methyl}-2,3,4,9-tetrahydro-1H-β-carboline-(3R)-(N-hydroxy)carboxamide Hydrochloride The expected product is obtained according to the same process as that described in Example 1 using, in Step A, the substrate used for Step A of Example 19 and using N-N-dimethyl-5-aminopentylamide as reagent in Step G.

EXAMPLE 21

6-Methoxy-2-[(4-methoxyphenyl)sulphonyl]-9-{[3-(N-ethyl)carbamoyl)propylcarbamoyl]methyl}-2,3,4,9-tetrahydro-1H-β-carboline-(3R)-(N-hydroxy)carboxamide Hydrochloride The expected product is obtained according to the same process as that described in Example 1 using, in Step A, the substrate used for Step A of Example 19 and using N-ethyl-4-aminobutylamide as reagent in Step G.

EXAMPLE 22

6-Hydroxy-2-[(4-methoxyphenyl)sulphonyl]-9-[(4-aminobutylcarbamoyl)methyl]-2,3,4,9-tetrahydro-1H-β-carboline-(3R)-(N-hydroxy)carboxamide Dihydrochloride The expected product is obtained according to the same process as that described in Example 1 using, in Step A, the substrate used for Step A of Example 18 and using 1,4-butyldiamine as reagent in Step G.

EXAMPLE 23

6-Methoxy-2-[(4-methoxyphenyl)sulphonyl]-9-{[6-(N,N-dimethyl)aminohexylcarbamoyl]methyl}-2,3,4,9-tetrahydro-1H-β-carboline-(3R)-(N-hydroxy)carboxamide The expected product is obtained according to the same procedure as in Example 1 using, in Step A, the substrate used for Step A of Example 19 and using N1,N1-dimethyl-1,6-hexyldiamine as reagent in Step G.

EXAMPLE 24

6-Methoxy-2-[(4-methoxyphenyl)sulphonyl]-9-{[2-(N-propyl)aminoethylcarbamoyl]methyl}-2,3,4,9-tetrahydro-1H-β-carboline-(3R)-(N-hydroxy)carboxamide Hydrochloride The expected product is obtained according to the same process as that described in Example 1 using, in Step A, the substrate used for Step A of Example 19 and using N1-propyl-1,2-ethyldiamine as reagent in Step G.

EXAMPLE 25

2-(4-Fluorobenzenesulphonyl)-9-[(3-morpholin-4-ylpropylcarbamoyl)methyl]-2,3,4,9-tetrahydro-1H-β-carboline-(3R)-(N-hydroxy)carboxamide The expected product is obtained according to the same process as that described in Example 1 using 4-fluorobenzenesulphonyl chloride as reagent in Step D.

EXAMPLE 26

2-[(4-Methoxyphenyl)sulphonyl]-9-{[3-(2-methylpiperidino)propylcarbamoyl]methyl}-2,3,4,9-tetrahydro-1H-β-carboline-(3R)-(N-hydroxy)carboxamide The expected product is obtained according to the same process as that described in Example 1 using 1-(3-aminopropyl)-2-pipecoline as reagent in Step E.

EXAMPLE 27

2-[(4-Methoxyphenyl)sulphonyl]-9-{[3-(hydroxysulphonyl)propylcarbamoyl]methyl}-2,3,4,9-tetrahydro-1H-β-carboline-(3R)-(N-hydroxy)carboxamide The expected product is obtained according to the same process as that described in Example 1 using 3-amino-1-propanesulphonic acid as reagent in Step E.

EXAMPLE 28

2-[(4-Methoxyphenylsulphonyl]-9-{[2-(2-aminoethoxy)ethylcarbamoyl]methyl}-2,3,4,9-tetrahydro-1H-β-carboline-(3R)-(N-hydroxy)carboxamide The expected product is obtained according to the same process as that described in Example 1 using 2-(2-aminoethoxy)-1-ethanamine as reagent in Step E.

EXAMPLE 29

2-[(4-Methoxyphenyl)sulphonyl]-9-[(3-morpholin-4-ylpropylcarbamoyl)ethyl]-2,3,4,9-tetrahydro-1H-β-carboline-(3R)-(N-hydroxy)carboxamide The expected product is obtained according to the same process as that described in Example 1 using tert-butyl 1-bromopropanoate as reagent in Step A.

Pharmacological Study of the Compounds of the Invention

EXAMPLE 30

Enzymatic Inhibition of Metalloproteinases

Four recombinant human enzymes MMP-1 (interstitial collagenase), MMP-2 (72 kDa gelatinase A), MMP-3

(stromelysin 1) and MMP-9 (92 kDa gelatinase B) are activated with APMA (4-aminophenylmercuric acetate).

The enzymatic tests are carried out using a peptidomimetic substrate:

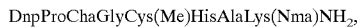

DnpProChaGlyCys(Me)HisAlaLys(Nma)NH$_2$, which is cleaved between the glycine and the cysteine to yield a fluorescent derivative (Anal. Biochem., 212, 58–64, 1993).

The reactions, carried out in a buffer of 50 mM Tris, 200 mM NaCl, 5 mM CaCl$_2$, 0.1% Brij 35 at pH 7.7, are initiated using 20 μM substrate in a total volume of 100 μl at 37° C. The fluorescence obtained after six hours is read in a 96-well plate in a fluorimeter equipped with a combination of 340 nm and 400 nm filters for excitation and emission.

In the tests, the compounds of the invention exhibited IC$_{50}$s of from 30 to 400 nM for the enzyme MMP-1, and of from 0.1 to 42 nM for the enzymes MMP-2, MMP-3 and MMP-9. More specifically, the compound of Example 2 exhibits an IC$_{50}$ of 32.6 nM for the enzyme MMP-1, and the compound of Example 11 exhibits IC$_{50}$s of 1.6 nM, 3.1 nM and 0.1 nM for the enzymes MMP-2, MMP-3 and MMP-9, respectively.

EXAMPLE 31

In Vitro Angiogenesis

Portions of thoracic aorta of male Fischer 344 rats aged from 8 to 12 weeks are immersed in a type I collagen gel according to the method of Nicosia et Ottinetti (1990). After five days of culture in a medium without serum, the preparations are examined using a microscope and the formation of pseudo-vessels is quantified in terms of vascular density after digitisation and image analysis.

By way of example, when tested at 1 μM the compounds of Examples 2, 13 and 15 result in inhibition of 50 to 100% neovascularisation.

EXAMPLE 32

Pharmaceutical Composition

Formulation for the preparation of 1000 tables each comprising 10 mg of active ingredient:

| | |
|---|---|
| Compound of Example 1 | 10 g |
| Hydroxypropyl cellulose | 2 g |
| Wheat starch | 10 g |
| Lactose | 100 g |
| Magnesium stearate | 3 g |
| Talc | 3 g |

We claim:
1. A compound selected from those of formula (I):

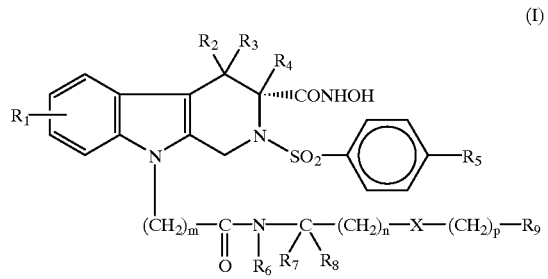

in which:
m represents 1 to 4 inclusive,
n and p, which may be the same or different, each represents, independently of the other, 0 to 4 inclusive,
X represent oxygen, sulphur, or a single bond,
R$_1$ represents hydrogen, halogen, linear or branched (C$_1$–C$_6$)alkyl, linear or branched (C$_1$–C$_6$)trihaloalkyl, hydroxy, linear or branched (C$_1$–C$_6$)alkoxy, or linear or branched (C$_1$–C$_6$)trihaloalkoxy,
R$_2$, R$_3$, and R$_4$, which may be the same or different, each represents, independently of the others, hydrogen or linear or branched (C$_1$–C$_6$)alkyl,
R$_5$ represent hydrogen, halogen, linear or branched (C$_1$–C$_6$)alkoxy, or aryloxy,
R$_6$, R$_7$, and R$_8$, which may be the same or different, each represents, independently of the others, hydrogen or linear or branched (C$_1$–C$_6$)alkyl, or together (R$_6$ and R$_7$, or R$_6$ and R$_8$) form, with the nitrogen carrying R$_6$ and the carbon carrying R$_7$ and R$_8$, a piperidine, the remaining group (R$_7$ or R$_8$, respectively) then having one or the other meanings given above,
R$_9$ represents any one of the following:
—SO$_3$H,
—CO$_2$R$_{10}$ wherein R$_{10}$ represents hydrogen or linear or branched (C$_1$–C$_6$)alkyl,
—CO—NR$_{11}$R$_{12}$ wherein R$_{11}$ and R$_{12}$, which may be the same or different, represent hydrogen or linear or branched (C$_1$–C$_6$)alkyl, or R$_{11}$ and R$_{12}$ together form, with the nitrogen carrying them, an optionally-substituted piperidine or morpholine,
—NR$_{13}$R$_{14}$ wherein R$_{13}$R$_{14}$, which may be the same or different, represent hydrogen or linear or branched (C$_1$–C$_6$)alkyl, or R$_{13}$ and R$_{14}$ together form, with the nitrogen carrying them, an optionally-substituted piperidine or morpholine
the term "optionally-substituted" as used in the foregoing meaning optionally substituted with one or more, identical or different, groups selected from halogen, linear or branched (C$_1$–C$_6$)alkyl, linear or branched (C$_1$–C$_6$) alkoxy, hydroxy, and amino optionally substituted by one or two linear or branched (C$_1$–C$_6$)alkyl groups which may be the same or different, and
the term "aryl", as used in aryloxy, being understood to mean a phenyl, naphthyl, dihydronaphthyl, or tetrahydronaphthyl group, each of which is optionally substituted by one or more, identical or different, groups selected from halogen, linear or branched (C$_1$–C$_6$) alkyl, linear or branched (C$_1$–C$_6$)trihaloalkyl, linear or branched (C$_1$–C$_6$)alkoxy, linear or branched (C$_1$–C$_6$) trihaloalkoxy, or hydroxy, and an isomer, and a pharmaceutically-acceptable addition salt thereof.

2. A pharmaceutical composition useful in the inhibition of neovascularization comprising as active principle an effective amount of a compound as claimed in claim 1, in combination with one or more pharmaceutically-acceptable excipients or carriers.

3. A compound of claim 1 which is 2-[(4-Methoxyphenyl)sulphonyl]-4-[(2-morpholin-4-ylethyl-carbamoyl)methyl]-2,3,4,9-tetrahydro-1H-β-carboline-(3R)-(N-hydroxy)carboxamide acetate.

4. A compound of claim 1 which is a 2-[(4-Methoxyphenyl)sulphonyl]-9-[(2-morpholin-4-ylethyl-carbamoyl)methyl]-2,3,4,9-tetrahydro-1H-β-carboline-(3R)-(N-hydroxy)carboxamide pharmaceutically-acceptable acid addition salt.

5. A compound of claim 1 which is 2-[(4-Methoxyphenyl)sulphonyl]-9-{[(2-(2-morpholin-4-ylethyl-sulphanyl)ethylcarbamoyl]methyl}-2,3,4,9-tetrahydro-1H-β-carboline-(3R)-(N-hydroxy)carboxamide hydrochloride.

6. A compound of claim 1 which is a 2-[(4-Methoxyphenyl)sulphonyl]-9-{[2-(2-morpholin-4-ylethyl-sulphanyl)ethylcarbamoyl]methyl}-2,3,4,9-tetrahydro-1H-β-carboline-(3R)-(N-hydroxy)carboxamide pharmaceutically-acceptable acid addition salt.

7. A compound of claim 1 which is 2-[(4-Methoxyphenyl)sulphonyl]-9-{[3-(2-morpholin-4-ylethyl-sulphanyl)propylcarbamoyl]methyl}-2,3,4,9-tetrahydro-1H-β-carboline-(3R)-(N-hydroxy)carboxamide Hydrochloride.

8. A compound of claim 1 which is a 2-[(4-Methoxyphenyl)sulphonyl]-9-{[3-(2-morpholin-4-ylethyl-sulphanyl)propylcarbamoyl]methyl}-2,3,4,9-tetrahydro-1H-β-carboline-(3R)-(N-hydroxy)carboxamide pharmaceutically-acceptable acid addition salt.

9. A compound of claim 1 which is 2-[(4-Methoxyphenyl)sulphonyl]-9-[N-methyl-(2-morpholin-4-ylethyl-carbamoyl)methyl]2,3,4,9-tetrahydro-1H-β-carboline-(3R)-(N-hydroxy)carboxamide hydrochloride.

10. A compound of claim 1 which is a 2-[(4-Methoxyphenyl)sulphonyl]-9-[N-methyl-(2-morpholin-4-ylethyl-carbamoyl)methyl]2,3,4,9-tetrahydro-1H-β-carboline-(3R)-(N-hydroxy)carboxamide pharmaceutically-acceptable acid addition salt.

11. A method for inhibition of neovascularization in a living body in need thereof comprising the step of administering to the living body an amount of a compound of claim 1 which is effective as a metalloproteinase and neovascularization inhibitor.

* * * * *

UNITED STATES PATENT AND TRADEMARK OFFICE
CERTIFICATE OF CORRECTION

PATENT NO. : 6,066,633          Page 1 of 1
DATED : May 23, 2000
INVENTOR(S) : G. De Nanteuil, G. Remond, J. Paladino, G. Atassi, A. Pierre, G. Tucker, J. Bonnet and M. Sabatini It is certified that error appears in the above-identified patent and that said Letters Patent is hereby corrected as shown below:

Column 4,
Line 18, "in which $R_2$," should read, -- in which $R_1$, --

Column 10,
Line 5, "3R) -" should read, -- (3R) --.

Column 17,
Line 9, "sulphonyl] -4-" should read, -- sulphonyl] -9- --.

Signed and Sealed this

Twenty-eighth Day of May, 2002

*Attest:*

JAMES E. ROGAN
*Attesting Officer*     *Director of the United States Patent and Trademark Office*